United States Patent [19]

Farin-Nia et al.

[11] Patent Number: 5,145,365

[45] Date of Patent: * Sep. 8, 1992

[54] GLASS ORTHODONTIC BRACKET

[75] Inventors: Farrokh Farzin-Nia, Inglewood, Calif.; Richard W. Petticrew, Odessa, Fla.

[73] Assignee: Ormco Corporation, Glendora, Calif.

[*] Notice: The portion of the term of this patent subsequent to Jul. 16, 2008 has been disclaimed.

[21] Appl. No.: 627,507

[22] Filed: Dec. 14, 1990

Related U.S. Application Data

[63] Continuation of Ser. No. 358,715, May 26, 1989, Pat. No. 5,032,081.

[51] Int. Cl.[5] .................................................. A61C 3/00
[52] U.S. Cl. .......................................................... 433/8
[58] Field of Search ..................... 433/8, 9; 501/3, 7; 106/35; 264/16

[56] References Cited

U.S. PATENT DOCUMENTS

| | | | |
|---|---|---|---|
| 3,490,984 | 1/1970 | Petticrew et al. | 428/410 |
| 4,784,606 | 11/1988 | Jones et al. | 433/9 |
| 4,789,649 | 12/1988 | Abert et al. | 501/3 |
| 4,814,297 | 3/1989 | Beall et al. | 501/7 |
| 4,988,293 | 1/1991 | Collins et al. | 433/8 |

*Primary Examiner*—John J. Wilson
*Attorney, Agent, or Firm*—Wood, Herron & Evans

[57] ABSTRACT

An orthodontic bracket made of a partially crystallized glass material and method for making same. The orthodontic bracket has a thin compressive outer crystalline layer.

4 Claims, 4 Drawing Sheets

GLASS ORTHODONTIC BRACKET

This is a continuation of application Ser. No. 358,715, filed on May 26, 1989, now U.S. Pat. No. 5,032,081.

BACKGROUND OF THE INVENTION

In the field of orthodontics there has been an increasing demand for brackets that are visually asthetic. In response to this need, various materials have been suggested for use as orthodontics brackets. Plastic materials have been found to be unsatisfactory due to their inability to provide the appropriate strength necessary for an orthodontic bracket. Various ceramic material have been suggested in the prior art. However, prior art brackets made from these materials are quite brittle and are subject to fracture. There has also been suggested orthodontic brackets made of single crystalline alumina or cubic zirconia. While these have been found to provide the strength necessary for use as an orthodontic bracket, they are relatively expensive materials, and are relatively difficult to machine due to their hardness and are subject to fracture due to their extreme hardness.

It has also been suggested to make orthodontic brackets from an ion exchange strengthened glass, such as illustrated and set forth in U.S. Pat. No. 4,784,606. This patent discloses strengthening the glass by subjecting it to an ion exchange reaction. The ion exchange treatment is carried out by emersing the glass bracket in a bath of molten salt at elevated temperatures above the strain point and below the softening point of the glass. The treatment time can vary from 2-24 hours. After it is removed from the bath, the bracket is washed clean of excessive salt. This, of course, adds substantial manufacturing cost. Additionally, the ion layer formed is very thin, and a result, is subject to early wear which can result in failure of the part due to stress risers that can form.

It has been further suggested in the prior art to produce orthodontic brackets of a glass ceramic having dual crystalline structure, such as illustrated in U.S. Pat. No. 4,789,649. This patent discloses a bracket structure having relatively large crystals covered by a layer of smaller, flat crystals. While this structure may provide increased strength, its central crystalline structure is relatively difficult to machine and is subject to fracture in the same manner as other crystalline type brackets of the prior art.

Applicants have invented an orthodontic bracket which is made of a relatively inexpensive glass which can provide the desired strength, is easy to manufacture, relatively resistant to fracture, and does not require bath solutions or cleaning operations in order to enhance the strength of the material.

SUMMARY OF THE INVENTION

In one aspect of the present invention there is provided an orthodontic bracket which includes a base portion having a tooth contacting surface and a body member. The body member includes walls defining an arch wire slot. The bracket is made of a glass material having a thin compressive outer crystalline layer.

In another aspect of the present invention, there is provided a method of making a glass orthodontic bracket having a outer compressive crystalline layer comprising the steps of:

(a) forming the bracket from a glass material which is crystallizable when subjected to a heat treatment process; and
(b) subjecting the bracket to a heat treatment wherein a thin surface layer of the bracket is crystallized.

DETAILED DESCRIPTION OF THE DRAWINGS

DETAILED DESCRIPTION OF THE INVENTION

Figure 1:
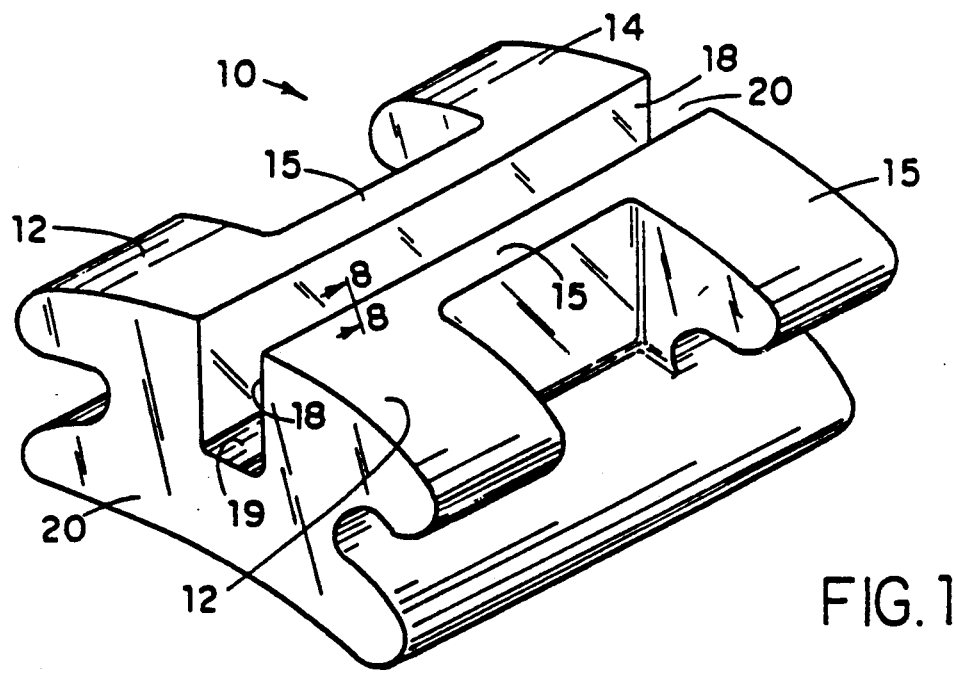
FIG. 1 illustrates a perspective view of an orthodontic bracket made in accordance with the present invention.

In referring to FIG. 1 there is illustrated an orthodontic bracket 10 made in accordance with the present invention. Bracket 10 comprises a pair of tie wings 12 and 14 respectively, which are supported by a base 20 having a tooth contact surface 21 for attachment to the tooth and a connecting portion 15 which connects tie wings 12, 14. The tie wings 12, 14 and connecting portion 15 form a pair of side walls 18 which form an aligned archwire slot 20 for receiving an orthodontic archwire (not shown) as is typically done in the prior art. A substantially flat bottom wall 19 connects side walls 18 and forms the bottom of slot 20. It should be understood that the bracket 10 may be of any desired configuration used in the art, with the one shown in FIG. 1 being for the purpose of illustration only.

Figure 2:
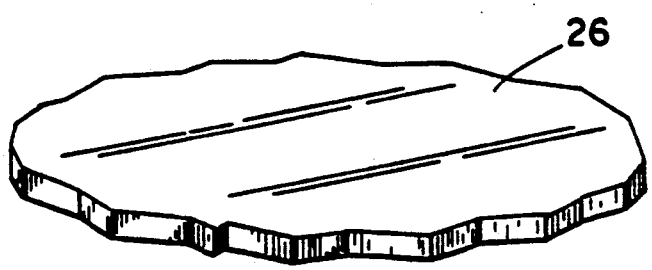
FIG. 2 is a perspective view of a portion of a glass plate from which the orthodontic bracket of FIG. 1 can be made.
Figure 3:
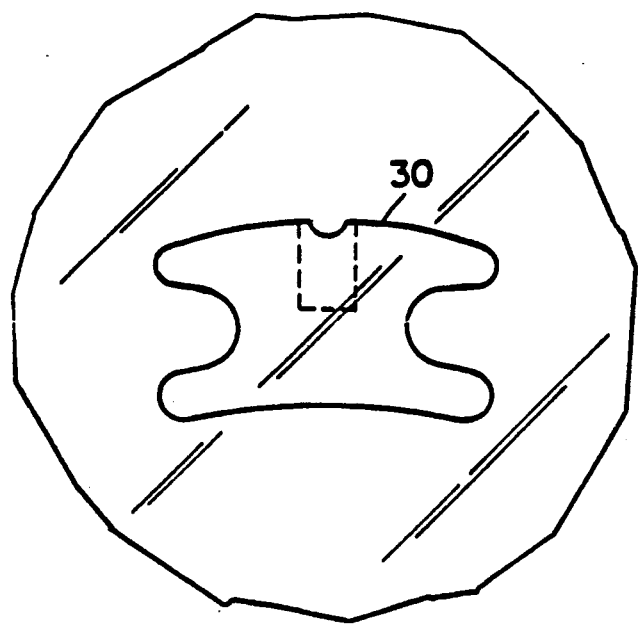
FIG. 3 is a top plan view of FIG. 2 illustrating, in solid line, the outline of an orthodontic bracket blank to be cut therefrom.
Figure 4:
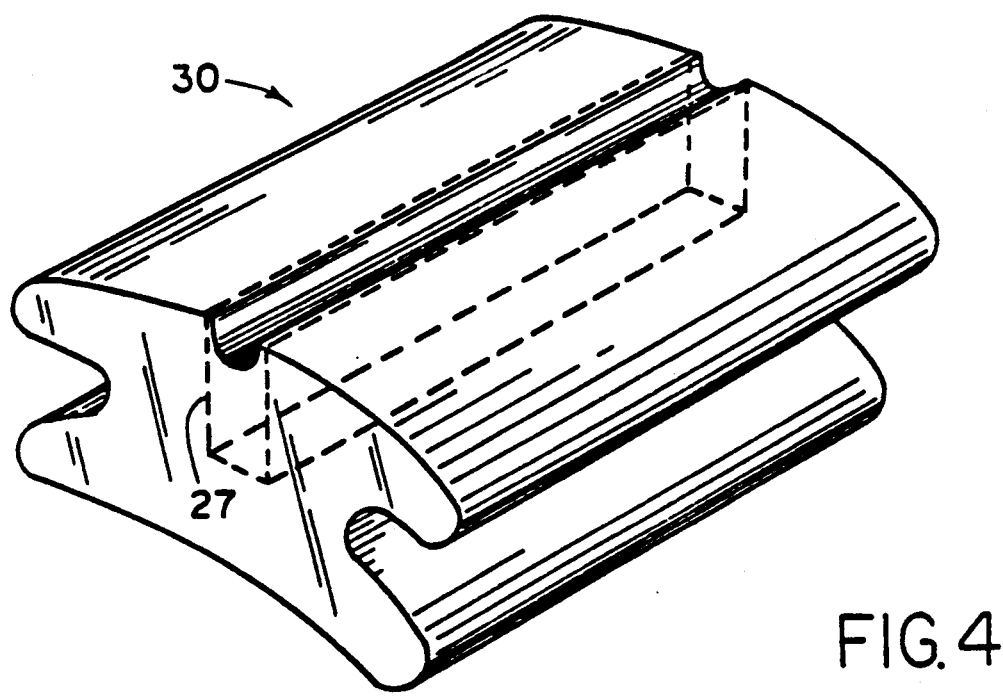
FIG. 4 is a perspective view of the orthodontic bracket blank cut from the plate illustrated in FIG. 3.
Figure 5:
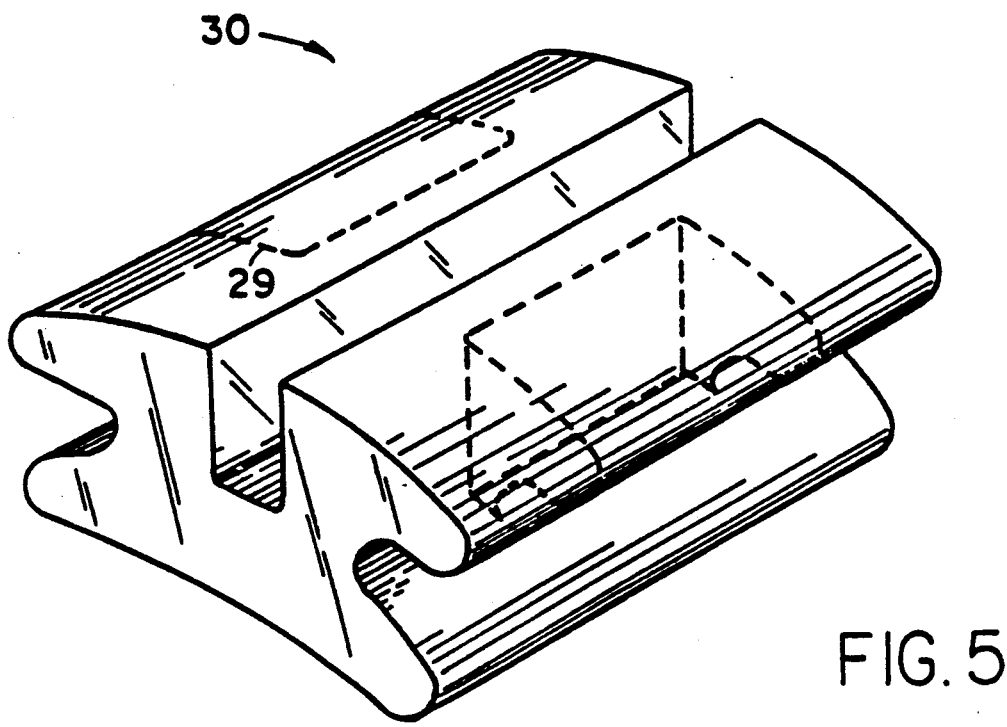
FIG. 5 is a perspective view of the bracket blank of FIG. 4, after the slot has been machined.
Figure 6:
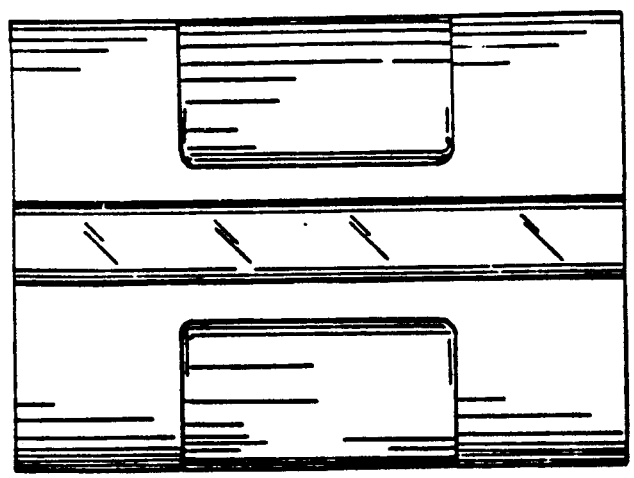
FIG. 6 is a top plain view of the orthodontic bracket after machining the notching illustrated by dash lines in FIG. 5.
Figure 7:
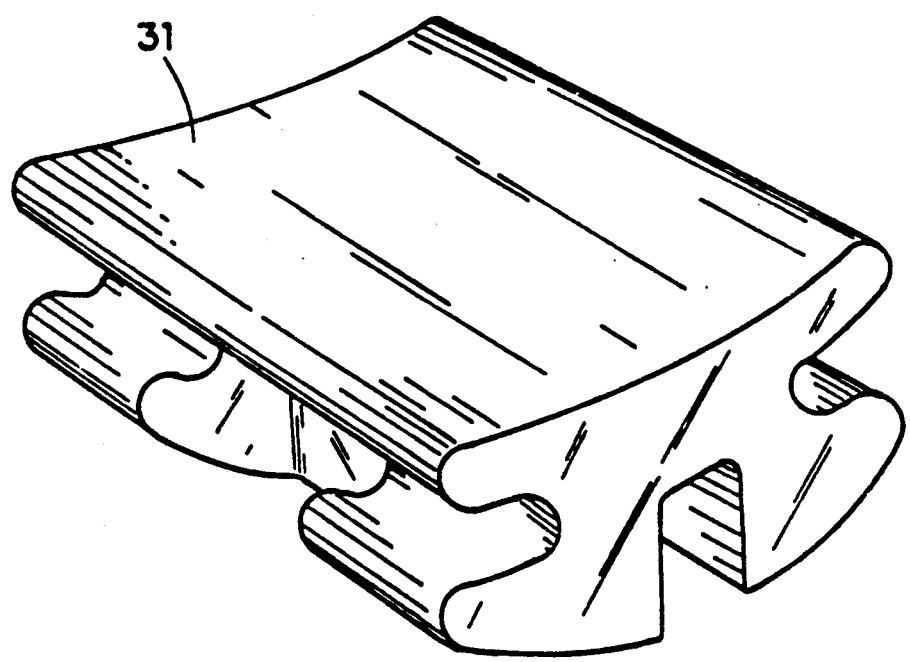
FIG. 7 is a bottom perspective of the bracket of FIG. 1.

The bracket 10 of the present invention is manufactured from a sheet of glass 26 provided in a sheet form as illustrated in FIG. 2. Referring to FIG. 3, there is illustrated, in solid line, the outline of an orthodontic bracket blank 30 to be cut from the plate 26. In the preferred form of the present invention, ultrasonic machining techniques are used to cut a plurality of individual bracket blanks 30 from plate 26. The bracket blank 30 cut therefrom, see FIG. 4, are then subjected to a plurality of further machining operations so as to form bracket 10. The dash line 27 indicates the outline of the slot 20 to be machined into bracket blank 30. In the present invention, the slot 20, is formed by diamond wheel grinding. The dashed lines 29 in FIG. 5 illustrate the next machining step to be conducted on bracket blank 30. In the next machining operation, the tie wings 12, 14 and connecting portions 15 are formed. In the preferred form of the present invention, diamond wheel cutting is used for this operation. Thereafter, ultrasonic machining is conducted on the bottom of the bracket blank 30 to finally form bracket 10 to form contact surface 31 for attachment to the tooth. In the preferred form of the present invention, ultrasonic machining techniques are used for cutting blanks 30 from plate 30 and forming contact surface 31. It is to be understood that various other machining techniques may be used in order to form the orthodontic bracket.

Figure 8:
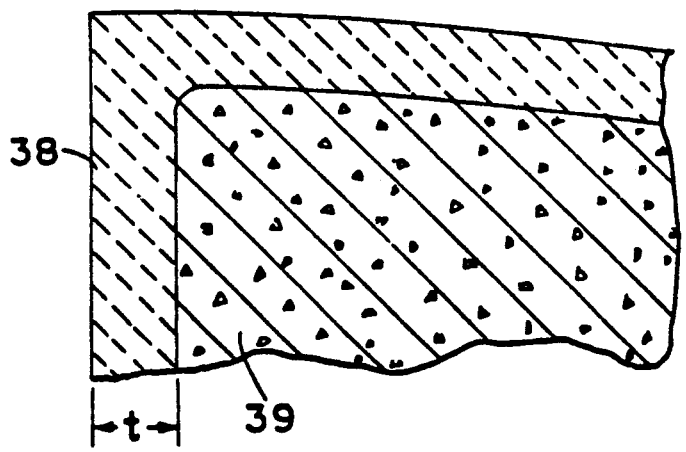
FIG. 8 is a greatly enlarged cross-sectional view of a portion of the bracket illustrated in FIG. 1 identified by dash lines 8—8.

After the bracket 10 has been finally formed, it is then subjected to a heat treatment process wherein a thin compressive crystalline outer layer 38 is formed on the surface of the bracket 10 as illustrated in FIG. 8. A glass composition that is useful in providing an outer crystalline layer consisting essentially of the following oxides in approximate weight percentages set forth below, exclusive of minor impurities:

TABLE I

| Material | Percentage | Preferred Percentages |
|---|---|---|
| $SiO_2$ | 55–70 | 56–63 |
| $Al_2O_3$ | 15–28 | 17–72 |
| $Z_nO$ | 0–14 | 10–14 |
| $Li_2O$ | 3–7 | 4–6 |
| $Na_2O$ | 0–7 | 1.5–5 |
| $Sb_2O_3$ | 0–2 | .5–2 |
| $K_2O$ | 0–3 | .1–1 |
| $BaO$ | 0–7 | — |
| $MgO$ | 0–5 | — |
| $T_1O_2$ | 0–.6 | — |

In the particular embodiment illustrated, a glass made from the following oxides in the appropriate weight percentage was used:

TABLE II

| Material | Percentage |
|---|---|
| $SiO_2$ | 58.8% |
| $Al_2O_3$ | 18.5% |
| $Z_nO$ | 12.5% |
| $Li_2O$ | 5.3% |
| $Na_2O$ | 3.3% |
| $Sb_2O_3$ | 1.5% |
| $K_2O$ | .1% |

The bracket 10 using the appropriate glass composition provides an inner amorphous portion 39 within the outer crystalline layer 38. The thin outer layer 38 does not substantially affect the clarity of the glass, thus, leaving the bracket substantially transparent or translucent. The thin crystalline layer 38 has a thickness t in the range of 0.0005 to 0.005 inches (0.0127–0.127 mm), preferably between about 0.003 to 0.005 inches (0.0762–0.127 mm). The outer crystalline layer 38 provides a compressive force on the surface, resulting in the substantial increase in the strength and fracture toughness of the bracket 10. The thickness t of layer 38 should not be too thick in relationship to the size of the product, as this can cause too great a compressive force to be produced which can result in failure of the part. The thickness t of layer 38 is preferably no greater than about 25% of the cross sectional thickness of the product at its thinnest point.

It is important in order to appropriately initiate the crystalline growth at the surface during the heat treatment process, that the surface have an appropriate roughness. Applicants found that the surface, after the machining operation should be no less than about 4 RMS (root means squared) and generally no greater than about 250 RMS. It is important that the crystallization formed during the heat treatment, initiate on the surface and not in the interior of the bracket 10, because if this happens, it will have the opposite result, that is, weakening of the bracket. If the surface finish is too smooth, crystalline growth may initiate internally of the product. Preferably the surface roughness is between about 30 to 125 RMS. Applicants have found that the particular orthodontic bracket 10 in FIG. 1, having the composition set forth in Table II, should be heated to a temperature in the range of 600°–800° C. It is important that the bracket 10 be heat treated under the optimal conditions to initiate crystallization on the surface. Applicants have found that the time and temperature required is sensitive to the particular composition being used. Thus, a little experimentation may be necessary for any particular composition being used to determine the appropriate time temperature necessary for crystallization. Generally, the higher the temperature, the shorter the time period necessary to obtain the thin outer crystalline layer 30. In the particular embodiment illustrated, Applicants have found that a heat treatment conducted at a temperature of about 700° C. for 1 to 2 hours provides the desired results.

Applicants have also found that the environment in which the brackets are heat treated can have a significant affect. For example, the orthodontic brackets are typically place in a boat, which is placed into an appropriate oven wherein it is heat treated. Apparatus have also found that the material of the boat and whether the boat is covered or not can have an effect upon its ultimate fracture toughness.

In an evaluation of fracture toughness in accordance with various heat treatment conditions, the fracture toughness was tested for specimens made out of the material from Table II, and tested for fracture toughness in accordance with ASTM-procedure. A control test specimen, identified as C, was made but not subjected to any heat treatment. A first test specimen (Sample 1) was made and subjected to a heat treatment process of 700° C. for about 1 hour which was heated in an aluminum oxide boat which was uncovered. Sample 2, a second test specimen, was heat treated for approximately 35 minutes in an aluminum oxide tray which was uncovered. Sample 3, a third test specimen, was heat treated at 690° C. for approximately 1 hour in an aluminum oxide tray which was uncovered. A fourth test specimen (Sample 4) was heat treated at 700° C. for approximately an hour in a stainless steel boat which was placed on bricks on its removal from the oven to be cooled. All Samples in No. 4 were fractured. It is important to place the bracket in a boat or tray having a thermal conductivity substantially similar to that of the material of the bracket. The following Table III sets forth a comparison of the fracture toughness of the control and heat treated specimens 1, 2, and 3 set forth above.

TABLE III

| Sample | Fracture Stress (m · Pa) | Fracture Toughness $K^{IC}$ (m · Pa · m) |
|---|---|---|
| C | 84 ± 18 | 1.1 ± 0.1 |
| 1 | 372 ± 70 | 4.6 ± 0.8 |
| 2 | 279 | 3.9 ± 1.8 |
| 3 | 268 ± 152 | 3.2 ± 1.8 |

As it can be seen from the foregoing, the first test specimen (Sample #1), i.e., which was heat treated for 60 minutes in an uncovered aluminum oxide tray, showed the greatest fracture toughness. Fracture toughness increased by a factor of approximately 4, as opposed to an unheat treated product. Thus, heat treating the bracket under appropriate conditions provided significant improvement in the fracture toughness of the material. As can be seen from sample #3, the 690° C. temperature simply did not provide the desired crystalline depth outer layer. Thus, it would appear that with this particular composition that the time and temperature used was insufficient to obtain the full fracture toughness capable of being obtained from the composition.

Applicants have compared orthodontic brackets made from the glass material of the present invention and heat treated in accordance with the present invention with brackets made of sapphire, cubic zirconium and polycrystalline aluminum materials of the prior art. As can be seen from the following Table IV below (values taken from a graphical representation and are only approximate), the brackets made out of the glass and heat treated according to the present invention, exhibited strength values equal to or better than sapphire and cubic zirconia, and markedly improved value over polycrystalline materials of the prior art. While the single crystal zirconia and alumina brackets showed a wide range of strength, approximately 20% of the brackets broke at values below acceptable levels. The strength of the glass materials was found to be more consistently high value, thus, providing more brackets in the acceptable strength range. Subjecting the glass bracket 10 to the heat treatment according to the present invention results in a complete change to the structure of the outer surface. The heat treatment provides a fresh new thin crystalline layer which has very few surface flaws, thus, minimizing or eliminating the effects of the machining conducted thereon.

TABLE IV

| Bracket Material Description | Relative Fracture Torque Values (Nm) |
|---|---|
| T.T. Glass | .07 |
| Sapphire | .065 |
| PCA | .045 |
| CZ | .07 |

It is to be understood that various modifications may be made to the present invention without departing from the scope thereof. For example, various other compositions may be used so long as the appropriate compressive crystalline outer layer may be formed. Other additives or impurities may be present which do not affect the structure or performance of the bracket. Another example of a composition believed to provide adequate performance is set forth below in Table V.

TABLE V

| Material | Percentage |
|---|---|
| $SiO_2$ | 61.8% |
| $Al_2O_3$ | 18.5% |
| $Z_nO$ | 12.5% |
| $Li_2O$ | 5.3% |
| $TiO_2$ | 1.0% |
| $Sb_2O_3$ | .5% |
| $Na_2O$ | .3% |
| $K_2O$ | .1% |

The present invention being limited by the following claims.

What is claimed is:

1. An orthodontic bracket including a base portion having a tooth contacting surface and a body member including walls defining an archwire slot, said bracket being made of an amorphous glass material and having an outer crystalline strengthening layer.

2. An orthodontic bracket according to claim 1 wherein said glass is made of the following composition consisting essentially of:

| Material | Percentage |
|---|---|
| $SiO_2$ | 61.8 |
| $Al_2O_3$ | 18.5 |
| $Z_nO$ | 12.5 |
| $Li_2O$ | 5.3 |
| $TiO_2$ | 1.0 |
| $Na_2O$ | .3 |
| $Sb_2O_3$ | .5 |
| $K_2O$ | .1 |

3. An orthodontic bracket according to claim 1 wherein said outer crystalline layer has a thickness in the range of about 0.0005 to 0.005 inches (0.0127–0.127 mm).

4. An orthodontic bracket according to claim 1 wherein said outer crystalline layer has a thickness in the range of about 0.0005 to 0.003 inches.

* * * * *